United States Patent [19]

Mori et al.

[11] Patent Number: 4,814,468

[45] Date of Patent: Mar. 21, 1989

[54] OPTICALLY ACTIVE CARBACYCLIN INTERMEDIATES AND PROCESSES FOR THE PREPARATION THEREOF

[75] Inventors: Kenji Mori, Tokyo; Masahiro Tsuji, Kawagoe, both of Japan

[73] Assignee: Nisshin Flour Milling Co., Ltd., Tokyo, Japan

[21] Appl. No.: 868,672

[22] Filed: May 30, 1986

[30] Foreign Application Priority Data

Jun. 4, 1985 [JP] Japan ................................ 60-119807

[51] Int. Cl.4 .......................................... C07D 317/72
[52] U.S. Cl. .................................... 549/336; 549/332
[58] Field of Search ............................... 549/336, 332

[56] References Cited

FOREIGN PATENT DOCUMENTS 2013661 8/1979 United Kingdom .

OTHER PUBLICATIONS

Kojima et al., "Total Synthesis of 9(O)-Methanoprostacyclin and its Isomers" in Tet. Lett., 39, pp. 3743–3746, (1978).

Shibasaki et al., "New Synthetic Routes to 9(O)-Methanoprostacyclin, A Highly Stable and Biologically Potent Analog of Prostacyclin" in Tet. Lett., 5, pp. 433–436, (1979).

Sankyo Co., Ltd., "Optical Resolution of Methanocyclin Intermediates" in *Chemical Abstracts*, 101, 191879e, (1984).

Hiroi et al., "Synthetic Studies on Iridoid Terpenes via Regioselective Sulfenylation of β-Ketoesters and Oxidative Cleavage of β-Thioalcohols—A Novel Synthetic Route to (±)-Loganin–" in *Chemistry Letters*, 4, pp. 559–562, (1981).

*Primary Examiner*—John W. Rollins
*Assistant Examiner*—W. Catchpole
*Attorney, Agent, or Firm*—Cushman, Darby & Cushman

[57] ABSTRACT

New intermediate, an optically active (1S,5R)-7,7-alkylenedioxy-2-alkoxycarbonylbicyclo[3.3.0]octan-3-one which is useful for the synthesis of an optically active carbacyclin. This intermediate is prepared, as a non-reduced compound, from a racemic compound, (1SR,5RS)-7,7-alkylenedioxy-2-alkoxycarbonyl-cis-bicyclo[3.3.0]octane-3-one, by treatment of the racemic compound with a microorganism. The microorganism has an ability of specifically reducing the keto group of the (1R,5S) epimer of the racemic compound.

2 Claims, No Drawings

OPTICALLY ACTIVE CARBACYCLIN INTERMEDIATES AND PROCESSES FOR THE PREPARATION THEREOF

FIELD OF THE INVENTION

This invention relates to a new intermediate, an optically active (1S,5R)-7,7-alkylenedioxy-2-alkoxycarbonylbicyclo[3.3.0]octan-3-one, which is useful for the synthesis of an optically active carbacyclin.

BACKGROUND OF THE INVENTION

Prostacyclin (PGI$_2$) of the following structure is of various pharamological effects including blood platelet agglutination inhibitory activity and vasodilation activity, and is considered to be promising for development of medicine. However, prostacyclin has such a drawback, on the other hand, that it is a very unstable compound.

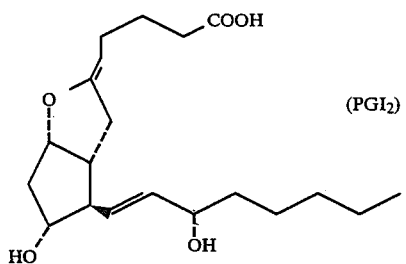

(PGI$_2$)

Of the prostacyclin derivatives, carbacyclin (called 9(O)-methanoprostacyclin) of the following structure has been known to be a chemically stable compound in which the oxygen atom of enol ether moiety of prostacyclin (PGI$_2$) is substituted with a methylene group.

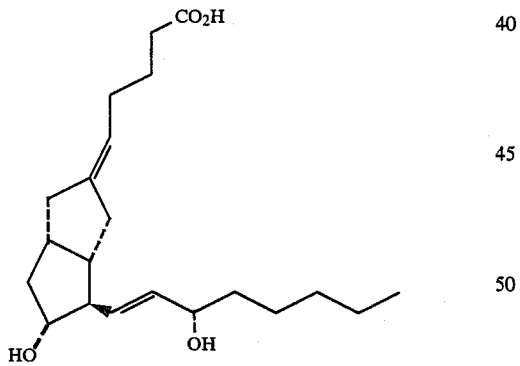

Processes for the synthesis of an optically active carbacyclin have been disclosed, for example, in "Tetrahedron", Vol. 37, 4391 (1981), "Journal of Organic Chemistry", Vol. 44, 2880 (1979) and "Journal of Organic Chemistry", Vol. 46, 1954 (1981). However, these processes are of the disadvantage of lengthy steps. Furthermore, processes for the synthesis of the above-mentioned carbacyclin using as an intermediate (1SR,5RS)-7,7-ethylenedioxy-2-ethoxycarbonyl-cis-bicyclo[3.3.-0]octan-3-one represented by the following formula (II)' are disclosed, for example, in "Tetrahedron Letters", 3743 (1978), "Journal of Chemical Society, Chemical Communication", 1067 (1978) and "Tetrahedron Letters", 433 (1979).

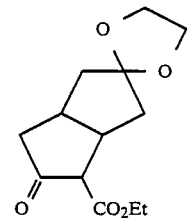

(II)'

However, the products obtained by the above-mentioned processes are racemic compounds, i.e., the (1SR,5RS) epimers which do not exhibit optical activity. That is, since the intermediates used in these processes are racemic compounds, the products obtained thereby are necessarily racemic compounds. Accordingly, if the optically active (1S,5R) compound can be used as the intermediate in the above-mentioned processes, it follows that the optically active carbacyclin referred to above is obtained quite conveniently.

It has been known in this connection that the above-mentioned intermediate, the compound of the formula (II)' is prepared from cis-bicyclo[3.3.0]octane-3,7-dione of the following formula (V)' according to the following scheme as taught in the above-mentioned "Journal of Chemical Society, Chemical Communication", 1067 (1978) and "Tetrahedron Letters", 433 (1979).

(V)'

SCHEME

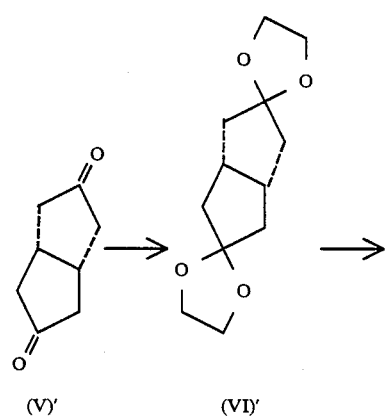

(V)'     (VI)'

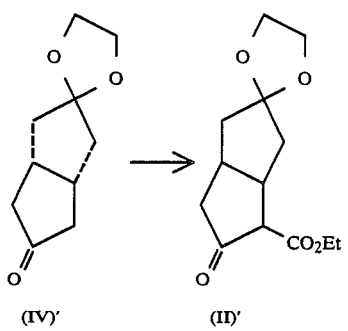

(IV)′ → (II)′

As can be seen from the above scheme, the compound of the formula (II)′ which is formed by introduction of an ethoxycarbonyl group into the compound of the formula (IV)′ always becomes a racemic compound which does not have optical activity. Thus, these prior art processes have involved such a decisive problem that because of very close similarities in chemical behavior and physical properties between the optically active substances constituting this racemic compound, i.e. the (1S,5R) epimer and the (1R,5S) epimer, the compound (II)′ cannot be resolved by means of an ordinary optical resolution. In this light, the (1S,5R) and (1R,5S) epimers can be said to be new substances which did not exist as an independently isolated compound.

Under such circumstances, we had come to such an idea that an optically active carbacyclin can be prepared by a simple process using only the (1S,5R) epimer, i.e. a compound represented by the following formula (I)′, if said (1S,5R) epimer can be isolated from the above-mentioned compound (II)′.

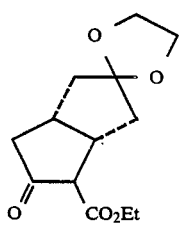

(I)′

After extensive researches, we have found that the simple process can be accomplished by a unique utilization of microorganisms.

DETAILED DESCRIPTION OF THE INVENTION

In accordance with one of the aspects of the present invention, there is provided a process which comprises treating (1SR,5RS)-7,7-alkylenedioxy-2-alkoxycarbonyl-cis-bicyclo[3.3.0]octan-3-one, which is a racemic compound of the following formula (II)

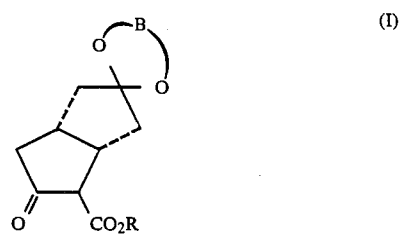

(II)

wherein R represents a lower alkyl group and B represents an alkylene group optionally substituted with alkyl, with a microorganism having an ability of specifically reducing the keto group of the (1R,5S) epimer of the racemic compound (II), thereby giving, as a non-reduced compound, optically active (1S,5R)-7,7-alkylenedioxy-2-alkoxycarbonylbicyclo[3.3.0]octan-3-one of the following formula (I)

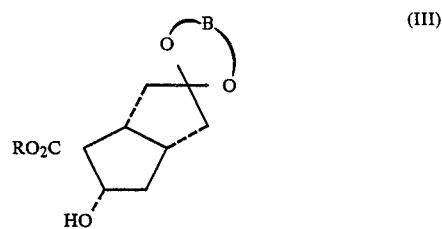

(I)

and, as a reduced compound, optically active (1S,5R,6R,7S)-3,3-alkylenedioxy-7-hydroxy-6-alkoxycarbonylbicyclo[3.3.0]octane of the following formula (III).

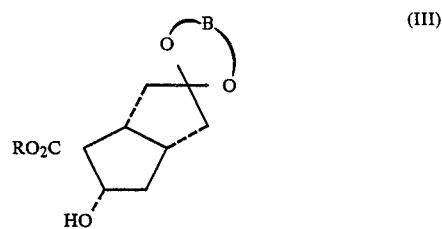

(III)

In accordance with another aspect of the present invention, there is provided a process which comprises further converting the compound of the formula (III) prepared by the above-mentioned process into the compound of the formula (II) which is then used for recycle as a starting compound for the synthesis of the compound of the formula (I), that is, the process wherein optically active (1S,5R,6R,7S)-3,3-alkylenedioxy-7-hydroxy-6-alkoxycarbonylbicyclo[3.3.0]octane of the formula (III) is subjected to oxidation reaction, thereby converting the hydroxy group thereof into the keto group and successively subjecting the thus oxidized compound to saponification and decarboxylation to yield 7,7-alkylenedioxy-cis-bicyclo[3.3.0]octan-3-one of the following formula (IV), and an alkoxycarbonyl group is then introduced into the 2-position of the compound of the formula (IV) to convert the compound (IV) into the racemic compound of the formula (II), (1SR,5RS)-7,7-alkylenedioxy-2-alkoxycarbonyl-cis-bicyclo[3.3.0]octan-3-one which is the starting compound for the synthesis of the compound of the formula (I).

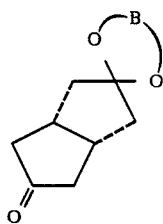
(IV)

From the fact that the compound of the formula (III) can be recycled for use in the compound of the formula (II) by the above-mentioned process of the present invention, it follows that the desired compound of the formula (I) can be increased in the overall yield.

Further, the present invention provides new intermediates prepared by the above-mentioned processes, which are optically active (1S,5R)-7,7-alkylenedioxy-2-alkoxy-carbonylbicyclo[3.3.0]octan-3-one of the formula (I)

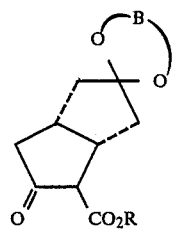
(I)

wherein R and B are as defined above, and (1S,5R,6R,7S)-3,3-alkylenedioxy-7-hydroxy-6-alkoxycarbonylbicyclo[3.3.0]octane of the formula (III)

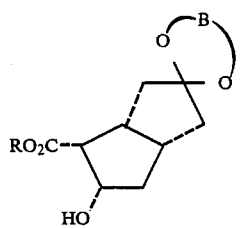
(III)

wherein R and B are as defined above.

In the compound (I)–(IV), concrete examples of the lower alkyl group as the substituent R include methyl, ethyl, propyl, i-propyl, n-butyl and i-butyl, and concrete examples of the alkylene group as the substituent B include ethylene, trimethylene and methyl-substituted ethylene.

The mixture comprising a non-reduced compound, (1S,5R)-7,7-alkylenedioxy-2-alkoxycarbonylbicyclo[3.3.0]octan-3-one (I) and a reduced compound, (1S,5R,6R,7S)-3,3-alkylenedioxy-7-hydroxy-6-alkoxycarbonylbicyclo[3.3.0]octane (III), which is obtained by the process of the present invention, can readily be separated by ordinary separation techniques such as extraction, absorption, chromatography, etc. From the viewpoint of easy handling, silica gel chromatography is preferably used.

The optically active (1S,5R)-7,7-ethylenedioxy-2-ethoxycarbonylbicyclo[3.3.0]octan-3-one (I) obtained by the present invention can be allowed to lead to an optically active carbacyclin which is the end product of the present invention, according to the following reaction scheme.

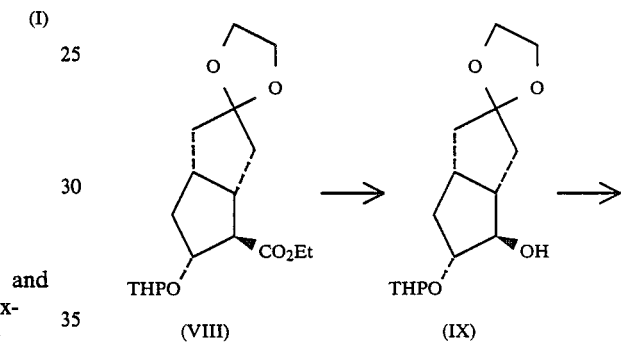

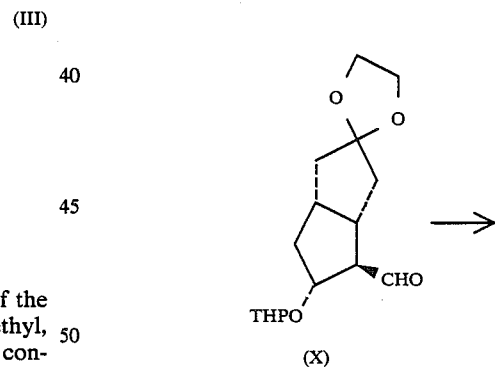

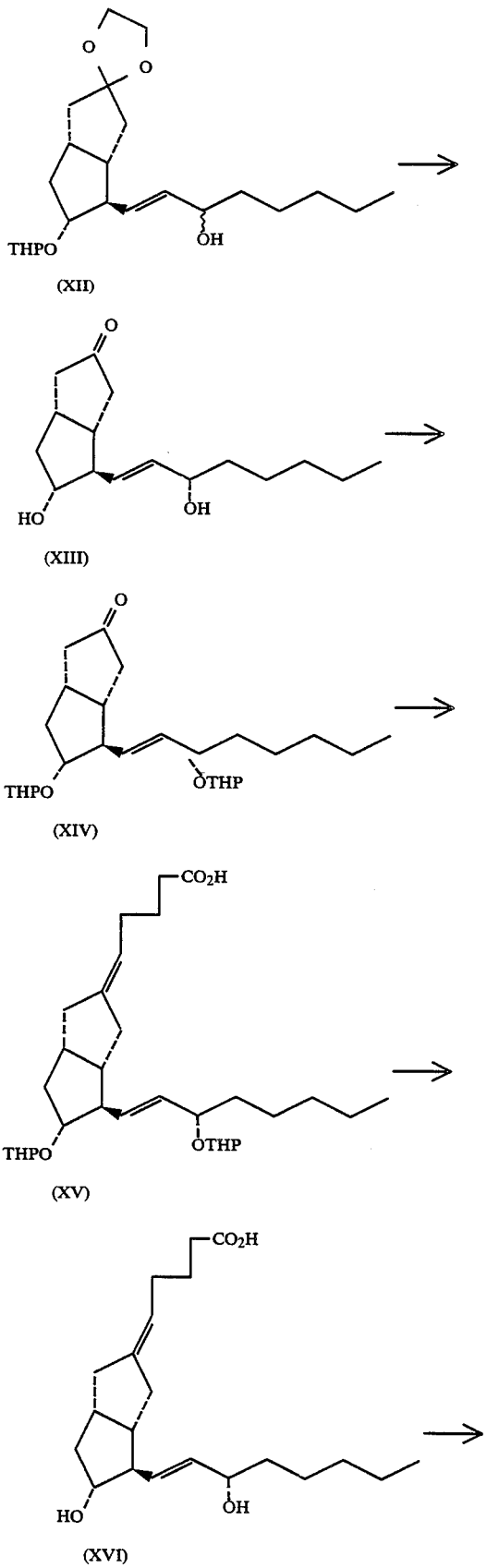

Accordingly, this new optically active intermediate (I) obtained by the present invention contributes greatly to economical synthesis of an optically active carbacyclin.

As shown in the above-mentioned reaction scheme, the material needed for the synthesis of an optically active carbacyclin is the (1S,5R) epimeric compound (I). Therefore, the compound (III) which is produced by selective reduction of the (1R,5S) epimer of the racemic compound (II) cannot be used directly for the synthesis of an optically active carbacyclin. Accordingly, it is an important technical and economical theme in the art to effectively utilize this compound (III) for the synthesis of an optically active carbacyclin. Taking this situation into account, we prosecuted extensive researches on the above-mentioned technical subject, and have eventually been successful in returning the compound of the formula (III) to the (1SR,5RS) compound of the formula (II) by a process which comprises converting the compound (III), by oxidation of the hydroxyl group to the keto group and the subsequent saponification and decarboxylation, into the 7,7-alkylenedioxy-cis-bicyclo[3.3.0]octan-3-one (IV) which is a precursor for the synthesis of the (1SR,5RS) compound (II), and subjecting this compound (IV) to reaction operation shown by the following scheme.

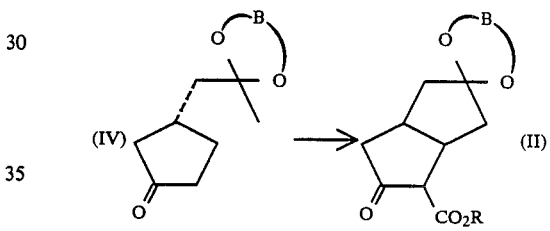

Recycle of the reduced compound (III) for use can attain a very great economical advantage in procuring the compound (II) which is the starting compound for the synthesis of the compound (I).

The oxidation of the hydroxyl group in the compound (III) to the keto group can be effected by the use of common chromic acid, for example, Collins reagent, Sarret reagent, Jones reagent, etc. The subsequent saponification and decarboxylation reaction may be carried out in water or a mixed solvent of water and appropriate alcohol using sodium hydroxide, potassium hydroxide or the like while suitably heating.

As the microorganism having an ability of specifically reducing the keto group of the (1R,5S) epimer of the racemic compound (1SR,5RS)-7,7-alkylenedioxy-2-alkoxycarbonyl-cis-bicyclo[3.3.0]octan-3-one (II), which is used in the present invention, there can be used a large number of microorganisms which have been known to be capable of converting by fermentation the keto group into the hydroxyl group. The preferred microorganisms are those belonging to a certain group of microorganism, for example which is called yeast. Examples of the yeast include genera Pichia and Saccharomyces, more particularly, strains such as *Saccharomyces cerevisiae, Saccharomyces uvarum, Saccharomyces carlsbergensis, Saccharomyces bailii* and *Pichia terricola.*

In the practice of the treatment of the compound (II) with the yeast, there may be used commercially available yeast and other yeast as collected from appropriate cultivation media in which they are cultivated. The treatment may be carried out by inoculating the yeast at 30°-37° C. in a buffer of pH 7 having dissolved therein a suitable carbon source, and then incubating the yeast with addition of a suspension of the compound (II) suspended in an appropriate suspension solution. The end point of the treatment at which the fermentation of the yeast is suspended is a point where the formation of the product is observed to reach a steady state by monitoring the amount of the product by means of thin chromatography or gas chromatography. After the completion of the treatment, the cells are removed, and the fermentation broth is saturated with common salt, extracted with a solvent, and the extract is purified by silica gel chromatography.

The present invention is illustrated in detail with reference to examples, but it should be construed that the invention is in no way limited to those examples. Examples 1-8 illustrate processes for obtaining the desired compound (I)' mentioned later by using the compound (II)', and Example 9 illustrates a partial process for recycling the compound (III)'. Referential Examples 1-2 illustrate processes for the synthesis of starting compounds, and Referential Examples 3-9 illustrate processes for the preparation of an optically active carbacyclin from the compound (I)'.

EXAMPLE 1

To a solution of 100 ml of 0.1M phosphate buffer (pH 7) containing sucrose (15 g) was dispersed 7.0 g of baker's yeast at 30° C., and the mixture was shaken at 30° C. for 15 minutes. To the resulting mixture was added an emulsion of 505 mg of (1SR,5RS)-7,7-ethylenedioxy-2-ethoxycarbonyl-cis-bicyclo[3.3.0]octan-3-one (II)' in 0.2% Triton X-100 solution (15 ml), and the mixture was shaken at 30° C. After 8 hours, 10 g of sucrose were added to the mixture. After shaking for 24 hours, the reaction mixture was filtered through Celite, the filtrate was saturated with sodium chloride and extracted three times with ethyl acetate. The organic layer was washed with saturated brine, dried over sodium sulfate, and concentrated. The residue was purified by silica gel chromatography (eluting solution: 20% (v/v) diethyl ether/n-hexane) to obtain 183 mg of oily (1S,5R)-7,7-ethylenedioxy-2-ethoxycarbonyl-bicyclo[3.3.0]octan-3-one, (I)' and 134 mg of oily (1S,5R,6R,7S)-3,3-ethylenedioxy-7-hydroxy-6-ethoxycarbonylbicyclo[3.3.0]octane, (III)'.

Specific rotation of (I)': $[\alpha]_D^{21}+15.3°$ (c=1.87, CHCl$_3$).

Infrared absorption (liquid-film method)(cm$^{-1}$): 1765, 1735, 1665, 1625.

Specific rotation of (III)': $[\alpha]_D^{21}+3.7°$ (c=1.48, CHCl$_3$).

Infrared absorption (liquid-film method)(cm$^{-1}$): 3550, 1720.

EXAMPLE 2

To a solution of 100 ml of 0.1M phosphate buffer (pH 7) containing sucrose (15 g) was dispersed 7.0 g of baker's yeast at 30° C., and the mixture was shaken at 30° C. for 15 minutes. To the resulting mixture was added an emulsion of 498 mg of (II)' in 0.2% Triton X-100 solution (15 ml) and the mixture was shaken at 30° C. To the mixture were added 10 g of sucrose after 8 hours and were added 10 g of sucrose and 3.5 g of baker's yeast after 24 hours and subsequently 48 hours. After shaking for 72 hours, substantially the same workup as in Example 1 gave 109 mg of (I)' and 76 mg of (III)'.

Specific rotation of (I)': $[\alpha]_D^{22}+19.9°$ (c=1.99, CHCl$_3$).

Specific rotation of (III)': $[\alpha]_D^{22}+3.8°$ (c=1.51, CHCl$_3$).

EXAMPLE 3

Four media of 100 ml (2% malt extract, 0.1% peptone, 2% glucose/purified water) placed in Sakaguchi flask were individually incubated with one platinum loop of *Saccharomyces cerevisiae* NCYC 240, and the flasks were shaken at 30° C. for 64 hours to effect pre-cultivation. Two portions of the four pre-cultivated media were then poured into medium of 1.8 l (having the same composition as mentioned above) in Erlenmeyer flask, and two flasks were shaken at 30° C. for 68 hours to effect cultivation. After collecting cells by centrifugation, the cells collected were added to 100 ml of 0.1M phosphate buffer containing 10 g of glucose kept at 30° C., and then shaken for 15 minutes. To the resulting mixture was then added an emulsion of 500 mg of (II)' in 0.2% Triton X-100 solution (15 ml), and the mixture was shaken at 30° C. and, after 6 hours, were added 10 g of glucose, and after 22 hours, were further added 5 g of glucose. After shaking 50 hours, the cells were removed from the reaction mixture by centrifugation, and a supernatant was saturated with sodium chloride and extracted three times with diethyl ether. The organic layer was washed with saturated brine and then dried over magnesium sulfate, and concentrated. The residue was purified by column chromatography (eluting solution: 20% (v/v) diethyl ether/n-hexane) to obtain 185 mg of (I)' and 133 mg of (III)'.

Specific rotation of (I)': $[\alpha]_D^{21}+13.2°$ (c=2.12, CHCl$_3$).

Specific rotation of (III)': $[\alpha]_D^{21}+3.7°$ (c=2.15, CHCl$_3$).

EXAMPLE 4

Following substantially the same procedure as described in Example 3, the reaction was initiated using *Saccharomyces uvarum* IFO 1225 cultivated in the same manner as in Example 3 and 504 mg of (II)'. To the reaction system was added glucose in such an amount as 10 g after 4 hours, 5 g after 19 hours and 10 g after 153 hours. After shaking for 167 hours, substantially the same workup as in Example 3 gave 101 mg of (I)' and 57 mg of (III)'.

Specific rotation of (I)': $[\alpha]_D^{21}+18.3°$ (c=1.87, CHCl$_3$).

Specific rotation of (III)': $[\alpha]_D^{21}+3.7°$ (c=1.32, CHCl$_3$).

EXAMPLE 5

Following substantially the same procedure as described in Example 3, the reaction was initiated using *Saccharomyces carlsbergensis* IFO 0565 cultivated in the same manner as in Example 3 and 500 mg of (II)'. To the reaction system were added 10 g of glucose after 4 hours and 10 g of glucose after 23 hours. After shaking for 68 hours, substantially the same workup as in Example 3 gave 219 mg of (I)' and 123 mg of (III)'.

Specific rotation of (I)': $[\alpha]_D^{21}+12.6°$ (c=2.08, CHCl$_3$).

Specific rotation of (III)': $[\alpha]_D^{21}+3.8°$ (c=1.47, CHCl$_3$).

EXAMPLE 6

Following substantially the same procedure as described in Example 3, the reaction was initiated using *Saccharomyces bailli* cultivated in the same media as in Example 3 (pre-cultivation for 22 hours, cultivation for 48 hours) and 511 mg of (II)′. In that case, however, the cultivation and reaction were carried out both at a temperature of 37° C. After shaking the reaction system for 5 hours, substantially the same workup gave 170 mg of (I)′ and 210 mg of (III)′.

Specific rotation of (I)′: $[\alpha]_D^{21}+23.9°$ (c=1.97, CHCl$_3$).

Specific rotation of (III)′: $[\alpha]_D^{21}+3.9°$ (c=1.81, CHCl$_3$).

EXAMPLE 7

Following substantially the same procedure as described in Example 3, the reaction was initiated (but at a reaction temperature of 37° C.) using *Pichia terricola* cultivated in the same manner as in Example 3 (but at a cultivation temperature of 37° C.) and 503 mg of (II)′. To the reaction system were added 10 g of glucose after 4 hours. After shaking the system for 20 hours, substantially the same workup as in Example 3 gave 80 mg of (I)′ and 90 mg of (III)′.

Specific rotation of (I)′: $[\alpha]_D^{21}+14.9°$ (c=2.67, CHCl$_3$).

Specific rotation of (III)′: $[\alpha]_D^{21}+4.0°$ (c=1.89, CHCl$_3$).

EXAMPLE 8

7,7-Ethylenedioxy-cis-bicyclo[3.3.0]octan-3-one (IV)′

A solution of 294 mg of (1S,5R,6R,7S)-3,3-ethylenedioxy-7-hydroxy-6-ethoxycarbonylbicyclo[3.3.0]octane (III)′ in methylene chloride (2 ml) as prepared in Example 1 was added to a solution of a chromic anhydride-pyridine complex in methylene chloride [prepared from chromic anhydride (688 mg), pyridine (1088 mg) and methylene chloride (18 ml)], and the mixture was stirred at room temperature for 10 minutes. The supernatant was separated, the residue was washed with ether, and the combined organic layer was extracted with 5% aqeuous sodium hydroxide solution. The aqueous layer was neutralized with dilute hydrochloric acid and extracted with ether. The organic layer was successively washed with saturated aqueous copper sulfate solution, saturated aqueous sodium hydrogencarbonate solution and saturated brine, dried over sodium sulfate, and concentrated to obtain 92 mg of (1R,5S)-7,7-ethylenedioxy-2-ethoxycarbonylbicyclo[3.3.0]octan-3-one. To the thus obtained (1R,5S)-7,7-ethylenedioxy-2-ethoxycarbonylbicyclo[3.3.0]octan-3-one were added 20 mg of sodium hydroxide and 0.9 ml of water-ethanol mixed solution (4:1), and the mixture was stirred at 90° C. for 4 hours. After cooling, the reaction mixture was neutralized with dilute hydrochloric acid and extracted with ether. The organic layer was then washed with saturated brine, dried over sodium sulfate, and concentrated to give 42 mg of the title compound.

Infrared absorption spectrum (liquid-film method) (cm$^{-1}$): 1740.

EXAMPLE 9

(1SR,5RS)-7,7-Ethylenedioxy-2-ethoxycarbonyl-cis-bicyclo[3.3.0]octan-3-one (II)′

A mixture of 14.1 g of 60% sodium hydride dispersed in mineral oil, 56.6 ml of diethyl carbonate and 60 ml of anhydrous benzene was heated under reflux in a nitrogen atmosphere. To the mixture was added dropwise over 3 hours and 30 minutes a solution of 21.4 g of 7,7-ethylenedioxy-cis-bicyclo[3.3.0]octan-3-one in 40 ml of anhydrous benzene, and reflux continued for 1 hour. After cooling, 20 ml of acetic acid and 150 ml of ice-water was added to the mixture, and the mixture was extracted three times with benzene. The organic layer was washed with water and saturated brine, dried over sodium sulfate, and concentrated. The residue was purified by silica gel chromatography (eluting solution: 17% (v/v) ethyl acetate/n-hexane) to obtain 24.0 g of the oily title compound.

Infrared absorption spectrum (liquid-film method) (cm$^{-1}$): 1765, 1735, 1665, 1625.

REFERENTIAL EXAMPLE 1

3,3,7,7-Diethylenedioxy-cis-bicyclo[3.3.0]octane (VI)′

A mixture of 30.0 g of cis-bicyclo[3.3.0]octane-3,7-dione, 145 ml of ethylene glycol, 1.19 g of p-toluenesulfonic acid and 800 ml of benzene was heated under reflux using Dean-Stark apparatus. The producing water was timely withdrawn from the mixture, benzene was added, and the reaction was effected for 5 hours. After cooling, the reaction mixture was washed with saturated aqueous sodium hydrogencarbonate solution and saturated brine, dried over sodium sulfate, and concentrated to obtain 50.7 g of the title compound of white crystals as the residue.

Infrared absorption spectrum (nujol method)(cm$^{-1}$): 1120.

REFERENTIAL EXAMPLE 2

7,7-Ethylenedioxy-cis-bicyclo[3.3.0]octan-3-one (IV)′

A mixture of 53.9 g of 3,3,7,7-diethylenedioxy-cis-bicyclo[3.3.0]octane as prepared in Referential Example 1, 2.26 g of p-toluenesulfonic acid and 500 ml of acetone-water (3:1) was stirred at room temperature for 1 hour and 40 minutes. Then, to the mixture was added 50 ml of saturated aqueous sodium hydrogencarbonate solution, the deposited crystals was filtered off and acetone was removed in vacuo from the filtrate, and the residue was extracted with chloroform. The organic layer was washed with saturated brine, dried over sodium sulfate, and concentrated. To the residue was added to 50 ml of a mixture of n-hexane/diethyl ether (1:1) and then crystals were deposited. After separating out the crystals by filtration, the filtrate was concentrated, and the residue was purified by silica gel chromatography (eluting solution: 20–30% (v/v) ethyl acetate/n-hexane) to obtain 20.4 g of the oily title compound.

Infrared absorption spectrum (liquid-film method) (cm$^{-1}$): 1740.

REFERENTIAL EXAMPLE 3

(1R,5S,6R,7R)-3,3-Ethylenedioxy-7-hydroxy-6-ethoxycarbonylbicyclo[3.3.0]octane (VII)

To a stirred solution of 2.09 g of (1S,5R)-7,7-ethylenedioxy-2-ethoxycarbonylbicyclo[3.3.0]octan-3-one (I)′ having $[\alpha]_D^{21}+23.9°$ (c=2.55, CHCl$_3$) in 21 ml of ethanol was added at −40° C. over 30 minutes 0.17 g of sodium borohydride. The mixture was stirred for 1 hour. After removal of ethanol in vacuo, the residue was diluted with water and extracted with ethyl acetate. The organic layer was washed with saturated brine, dried over sodium sulfate, and concentrated. The residue was purified by silica gel chromatography (eluting solution: 20–50% (v/v) diethyl ether/n-hexane) to obtain 1.60 g of the oily title compound.

Infrared absorption spectrum (liquid-film method) (cm$^{-1}$): 3500, 1730.

Specific rotation: $[\alpha]_D^{21} +26.1°$ (c=1.84, CHCl$_3$).

REFERENTIAL EXAMPLE 4

(1R,5S,6S,7R)-3,3-Ethylenedioxy-7-(2'-tetrahydropiranyloxy)-6-hydroxymethylbicyclo[3.3.0]octane (IX)

A mixture of 2.65 g of (1R,5S,6R,7R)-3,3-ethylenedioxy-7-hydroxy-6-ethoxycarbonylbicyclo[3.3.0]octane, 1.34 g of dihydropyrane, 0.26 g of pyridinium p-toluenesulfonate in 30 ml of anhydrous methylene chloride was stirred at room temperature for 3 hours. Then, the reaction mixture was successively washed with saturated aqueous sodium hydrogencarbonate solution and saturated brine, dried over sodium sulfate, and concentrated to obtain as the residue 3.70 g of oily tetrahydropyranyl ether (VIII). A solution of the resulted crude tetrahydropyranyl ether in 15 ml of anhydrous diethyl ether was added dropwise over 1 hour to a stirred and ice-cooled suspension of 0.59 g of lithium aluminum hydride in 50 ml of anhydrous diethyl ether. The mixture was further stirred at room temperature for 30 minutes. Adfter ice-cooling, to the reaction mixture was added successively 0.6 ml of water, 1.8 ml of 10% aqueous sodium hydroxide solution and 0.6 ml of water, and the mixture was further stirred for 1 hour. The mixture was filtered through Celite, dried over sodium sulfate, and concentrated. The residue was purified by silica gel chromatography (eluting solution: 25% (v/v) ethyl acetate/n-hexane) to obtain 3.04 g of the oily title compound.

Infrared absorption spectrum (liquid-film method) (cm$^{-1}$): 3470.

REFERENTIAL EXAMPLE 5

(1R,5S,6R,7R)-3,3-Ethylenedioxy-7-(2'-tetrahydropyranyloxy)-6-[(E)-3'-oxo-1'-octenyl]bicyclo[3.3.0]octane (XI)

A mixture of 3.04 g of (1R,5S,6S,7R)-3,3-ethylenedioxy-7-(2'-tetrahydropyranyloxy)-6-hydroxymethylbicyclo[3.3.0]octane as prepared in Referential Example 4, 4.40 g of pyridinium chlorochromate, 0.34 g of sodium acetate in 45 ml of anhydrous methylene chloride was stirred at room temperature for 3 hours. Then, the supernatant was separated, the residue was washed with diethyl ether, the combined organic layer was passed through a short column of Florisil, and concentrated to obtain 2.67 g of crude aldehyde (X) as the residue. To a stirred suspension of 0.38 g of 60% sodium hydride dispersed in mineral oil in 50 ml of anhydrous tetrahydrofuran was added dropwise over 10 minutes a solution of 2.20 g of dimethyl 2-oxoheptylphosphonate in 6 ml of anhydrous tetrahydrofuran at room temperature under argon, and the resulting mixture was stirred for 30 minutes. To the resultant mixture was added dropwise over 15 minutes at room temperature a solution of 2.67 g of the crude aldehyde in 6 ml of anhydrous tetrahydrofuran, and the mixture was stirred for 30 minutes. The reaction mixture was passed through a short column of silica gel, and concentrated. The residue was purified by silica gel chromatography (eluting solution: 10% (v/v) ethyl acetate/n-hexane) to obtain 2.62 g of the oily title compound.

Infrared absorption spectrum (liquid-film method) (cm$^{-1}$): 1695, 1670, 1630

REFERENTIAL EXAMPLE 6

(1R,5S,6R,7R)-7-Hydroxy-6-[(E)-3'α-hydroxy-1'-octenyl]bicyclo[3.3.0]octan-3-one (XIII)

To a solution of 3.34 g of (1R,5S,6R,7R)-3,3-ethylenedioxy-7-(2'-tetrahydropyranyloxy-6-[(E)-3'-oxo-1'-octenyl]-bicyclo[3.3.0]octane in 50 ml of methanol was added 0.16 g of sodium borohydride at −15° C., and the mixture was stirred for 30 minutes. Then, methanol was removed in vacuo, and saturated brine was added to the residue and the mixture was extracted with ethyl acetate, whereby the compound (XII) was formed. After removal of the solvent, to the residue was added 50 ml of a mixed solution of acetic acid-water-tetrahydrofuran (3:1:1) and the mixture was stirred at 45° C. for 3 hours. Then, the reaction mixture was diluted with saturated brine and extracted with ethyl acetate. The organic layer was successively washed with water, saturated aqueous sodium hydrogen carbonate solution and saturated brine, dried over sodium sulfate and concentrated. The residue was purified by silica gel chromatography (eluting solution: 20% (v/v) acetone-methylene chloride) to obtain 0.74 g of an oily substance (the 3'β epimer) from the less polar fraction and 0.96 g of the oily title compound (the 3'α epimer) from the more polar fraction.

Infrared absorption spectrum (liquid-film method) (cm$^{-1}$): 3420, 1740.

Specific rotation: $[\alpha]_D^{23} -8.2°$ (c=1.53, CHCl$_3$).

REFERENTIAL EXAMPLE 7

(1R,5S,6R,7R)-7-(2'-Tetrahydropyranyloxy)-6-[(E)-3'α-(2'-tetrahydropyranyloxy)-1'-octenyl]bicyclo[3.3.0]octan-3-one A mixture of 698 mg of (1R,5S,6R,7R)-7-hydroxy-6-[(E)-3'α-hydroxy-1'-octenyl]bicyclo[3.3.0]octan-3-one as prepared in Referential Example 6, 661 mg of dihydropyrane, 132 mg of pyridinium p-toluenesulfonate in 15 ml of anhydrous methylene chloride was stirred at room temperature for 3 hours. Then, the reaction mixture was successively washed with saturated sodium hydrogencarbonate solution and saturated brine, dried over sodium sulfate and concentrated. The residue was purified by silica gel chromatography (eluting solution: 10–20% (v/v) ethyl acetate/n-hexane) to obtain 1059 mg of the oily title compound.

Infrared absorpotion spectrum (liquid-film method) (cm$^{-1}$): 1745.

REFERENTIAL EXAMPLE 8

5(E)-Carbacyclin bis(tetrahydropyranyl)ether

To a solution of dimethyl sulfoxide anion (prepared from 409 mg of 60% sodium hydride dispersed in mineral oil and 5.3 ml of dimethyl sulfoxide) was added a solution of 2.27 g of (4-carboxybutyl)triphenylphosphonium bromide in dimethyl sulfoxide (5.3 ml), and the mixture was stirred at room temperature for 30 minutes under argon. To the resultant ylide solution was added a solution of 222 mg of (1R,5S,6R,7R)-7-(2'-tetrahydropyranyloxy)-6-[(E)-3'α-(2''-tetrahydropyranyloxy)-1'-octenyl]-bicyclo[3.3.0]octan-3-one in dimethyl sulfoxide (0.5 ml), and the mixture was stirred at 45° C. for 22 hours. Then, the mixture was charged with water and then acetic acid, and extracted with ether. The organic layer was washed with water and then saturated brine, dried over magnesium sulfate, and concentrated. The residue was purified by silica gel chromatography (eluting solution: 15% (v/v) ethyl acetate/n-hexane) to obtain 41 mg of an oily substance (the 5 Z isomer) from the less polar fraction and 100 mg of the oily title compound from the more polar fraction.

Infrared absorption spectrum (liquid-film method) (cm$^{-1}$): 1745, 1715.

REFERENTIAL EXAMPLE 9

5(E)-Carbacyclin

A mixture of 206 mg of 5(E)-carbacylin bis(tetrahydropyranyl)ether as prepared in Referential Example 8 in 8 ml of a mixed solution of acetic acid-water-tetrahydropyrane (3:1:1) was stirred at 45° C. for 3 hours. Then, the reaction mixture was diluted with saturated brine and extracted with ethyl acetate. The organic layer was washed with saturated brine, dried over magnesium sulfate, and concentrated. The residue was purified by silica gel chromatography (eluting solution: 50% (v/v) ethyl acetate/n-hexane) to obtain 82 mg of the crystalline title compound. Recrystallization from diethyl ether/n-hexane gave crystals, m.p. 58.5°–60.0° C.

Infrared absorption spectrum (KBr method) (cm$^{-1}$): 3380, 1725, 1680.

Specific rotation: $[\alpha]_D^{21} +89°$ (c=0.525, MeOH).

What is claimed is:

1. An optically active (1S,5R)-7,7-alkylenedioxy-2-alkoxycarbonylbicyclo[3.3.0]octan-3-one of the formula (I)

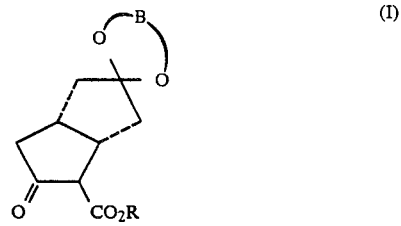

wherein R represents a lower alkyl and B represents an alkylene group optionally substituted with alkyl.

2. An optically active (1S,5R,6R,7S)-3,3-alkylenedioxy-7-hydroxy-6-alkoxycarbonylbicyclo[3.3.0]octane of the formula (III)

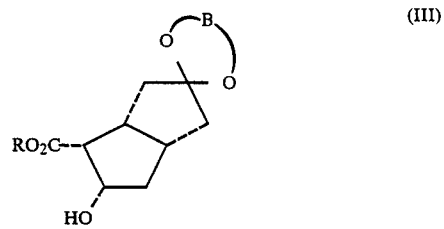

wherein R and B are as defined in claim 1.

* * * * *